(12) United States Patent
Imagawa (10) Patent No.: US 8,828,206 B2
(45) Date of Patent: Sep. 9, 2014

(54) GAS SENSOR ELEMENT AND GAS SENSOR EMPLOYING THE GAS SENSOR ELEMENT

(75) Inventor: Hirokatsu Imagawa, Obu (JP)

(73) Assignee: Denso Corporation, Kariya (JP)

( * ) Notice: Subject to any disclaimer, the term of this patent is extended or adjusted under 35 U.S.C. 154(b) by 288 days.

(21) Appl. No.: 13/486,031

(22) Filed: Jun. 1, 2012

(65) Prior Publication Data

US 2012/0305397 A1 Dec. 6, 2012

(30) Foreign Application Priority Data

Jun. 3, 2011 (JP) .................. 2011-125572

(51) Int. Cl.
*G01N 27/407* (2006.01)
*G01N 27/409* (2006.01)
(52) U.S. Cl.
CPC ..................... *G01N 27/409* (2013.01)
USPC ............... 204/427; 204/424; 204/426
(58) Field of Classification Search
None
See application file for complete search history.

(56) References Cited

U.S. PATENT DOCUMENTS

2007/0144905 A1* 6/2007 Tsuji et al. ............. 204/424

FOREIGN PATENT DOCUMENTS

| JP | 2007-199046 | 8/2007 |
|---|---|---|
| JP | 2007-206055 | 8/2007 |
| JP | 2009-130889 | 6/2009 |
| JP | 2010-181241 | 8/2010 |
| JP | 2010-256112 | 11/2010 |
| JP | 2010-276530 | 12/2010 |
| JP | 2011-089796 | 5/2011 |
| JP | 2011-123004 | 6/2011 |
| WO | WO 2010/136859 | 12/2010 |

* cited by examiner

*Primary Examiner* — J. Christopher Ball
(74) *Attorney, Agent, or Firm* — Nixon & Vanderhye PC (57) ABSTRACT

In a gas sensor element, a measurement gas is introduced to a measurement electrode through a porous diffusion-resistant layer. A catalyst layer is formed on an outer surface of the diffusion-resistant layer via which the measurement gas flows into the diffusion-resistant layer. In the catalyst layer, the percentage content of Pt is in the range of 2.5 to 12 mass %, the percentage content of Pd is in the range of 0.4 to 2 mass %, and the percentage content of Rh is in the range of 0.06 to 1.5 mass %. The catalyst layer includes catalytic noble metal particles each of which is made of an alloy that contains at least Pt. For each of the catalytic noble metal particles, the percentage content of Pt at an outer peripheral portion of the catalytic noble metal particle is lower than that at a core portion of the catalytic noble metal particle.

6 Claims, 6 Drawing Sheets

| SAMPLE | CATALYST LAYER | | | | PARTICLES Pt AT CORE PORTIONS (MASS%) | LEAN→RICH RESPONSE DELAY (ms) | EVALU-ATION | RICH→LEAN RESPONSE DELAY (ms) | EVALU-ATION | OUTPUT DEVIATION | EVALU-ATION | TOTAL EVALU-ATION |
|---|---|---|---|---|---|---|---|---|---|---|---|---|
| | Pt (MASS%) | Pd (MASS%) | Rh (MASS%) | Pt+Pd+Rh (MASS%) | | | | | | | | |
| A1 | 2.4 | 0.3 | 0.05 | 2.75 | 75 | 5 | ◎ | 5 | ◎ | 0.31 | × | × |
| A2 | 2.5 | 0.4 | 0.06 | 2.96 | 75 | 5 | ◎ | 5 | ◎ | 0.27 | ○ | ○ |
| A3 | 2.5 | 0.4 | 0.2 | 3.1 | 75 | 5 | ◎ | 5 | ◎ | 0.26 | ○ | ○ |
| A4 | 2.5 | 0.4 | 0.3 | 3.2 | 75 | 10 | ◎ | 5 | ◎ | 0.26 | ○ | ○ |
| A5 | 2.5 | 0.4 | 1.5 | 4.4 | 75 | 24 | ○ | 5 | ◎ | 0.22 | ◎ | ○ |
| A6 | 2.5 | 0.4 | 1.6 | 4.5 | 75 | 28 | × | 5 | ◎ | 0.22 | ◎ | × |
| A7 | 2.5 | 0.8 | 0.06 | 3.36 | 75 | 5 | ◎ | 12 | ◎ | 0.25 | ○ | ○ |
| A8 | 2.5 | 1.2 | 0.06 | 3.76 | 75 | 5 | ◎ | 30 | ◎ | 0.23 | ○ | ○ |
| A9 | 2.5 | 2 | 0.06 | 4.56 | 75 | 5 | ◎ | 45 | ○ | 0.21 | ◎ | ○ |
| A10 | 2.5 | 2.1 | 0.06 | 4.66 | 75 | 5 | ◎ | 52 | × | 0.2 | ◎ | × |
| A11 | 3 | 0.8 | 0.2 | 4 | 75 | 5 | ◎ | 12 | ◎ | 0.22 | ◎ | ◎ |
| A12 | 3.75 | 1.0 | 0.25 | 5 | 75 | 7 | ◎ | 23 | ◎ | 0.19 | ◎ | ◎ |
| A13 | 4.5 | 1.2 | 0.3 | 6 | 75 | 10 | ◎ | 30 | ◎ | 0.18 | ◎ | ◎ |
| A14 | 12 | 2 | 1.5 | 15.5 | 75 | 24 | ○ | 45 | ○ | 0.12 | ◎ | ○ |
| A15 | 12.1 | 2.1 | 1.6 | 15.8 | 75 | 28 | × | 52 | × | 0.11 | ◎ | × |
| A16 | 4.5 | 1.2 | 0.3 | 6 | 65 | 10 | ◎ | 30 | ◎ | 0.19 | ◎ | ◎ |
| A17 | 4.5 | 1.2 | 0.3 | 6 | 60 | 10 | ◎ | 30 | ◎ | 0.23 | ○ | ○ |
| A18 | 4.5 | 1.2 | 0.3 | 6 | 50 | 10 | ◎ | 30 | ◎ | 0.24 | ○ | ○ |
| A19 | 2.54 | 0.4 | 0.06 | 3 | 50 | 5 | ◎ | 5 | ◎ | 0.28 | ○ | ○ |
| A20 | 4.5 | 1.2 | 0.3 | 6 | 45 | 10 | ◎ | 30 | ◎ | 0.35 | × | × |
| A21 | 12 | 2 | 1.5 | 15.5 | 45 | 24 | ○ | 45 | ○ | 0.29 | × | × |

GAS SENSOR ELEMENT AND GAS SENSOR EMPLOYING THE GAS SENSOR ELEMENT

CROSS-REFERENCE TO RELATED APPLICATION

This application is based on and claims priority from Japanese Patent Application No. 2011-125572, filed on Jun. 3, 2011, the content of which is hereby incorporated by reference in its entirety into this application.

BACKGROUND

1. Technical Field

The present invention relates to a gas sensor element for sensing the concentration of a specific component in a gas to be measured (to be simply referred to as a measurement gas hereinafter) and to a gas sensor that employs the gas sensor element.

2. Description of Related Art

In recent years, from the viewpoint of global environmental protection, the availability of gasoline direct-injection engines and alternative fuel engines, such as CNG (Compressed Natural gas) engines, has been investigated. Accordingly, gas sensors for use in combustion control of the gasoline direct-injection engines and alternative fuel engines have become a focus of attention.

As gas sensor elements to be incorporated in those gas sensors, there are known ones which include: a solid electrolyte body having oxygen ion conductivity and an opposite pair of first and second surfaces; a measurement electrode provided on the first surface of the solid electrolyte body so as to be exposed to a measurement gas; a reference electrode provided on the second surface of the solid electrolyte body so as to be exposed to a reference gas; and a porous diffusion-resistant layer through which the measurement gas is introduced to the measurement electrode.

However, the known gas sensor elements have the following problem when the measurement gas is exhaust gas from an internal combustion engine of a motor vehicle.

Since hydrogen ($H_2$) has a smaller molecular weight than oxygen ($O_2$), the flowing speed of hydrogen contained in the exhaust gas through the diffusion-resistant layer is higher than that of oxygen contained in the same. Consequently, the hydrogen reaches the measurement electrode earlier than the oxygen, so that the partial pressure of oxygen at the measurement electrode becomes lower than the actual partial pressure of oxygen in the exhaust gas. As a result, the output (e.g., the output current or the output voltage) of the gas sensor element is deviated from the correct value that represents the actual concentration of oxygen in the exhaust gas.

In particular, in the case of the engine being a gasoline direct-injection engine, during its operation (including starting operation), the engine tends to generate more hydrogen than a conventional gasoline engine due to the difference in combustion mechanism therebetween. Moreover, in the case of the engine being a CNG engine, during its operation, the engine also tends to generate more hydrogen than a conventional gasoline engine due to the difference in composition between CNG and gasoline. Therefore, in both the cases, the output deviation of the gas sensor element due to the hydrogen contained in the exhaust gas may be significant.

To solve the above problem, there is disclosed a technique in, for example, Japanese Patent Application Publications No. 2007-199046 and No. 2010-276530. According to the technique, a porous catalyst layer is formed on the outer surface of the diffusion-resistant layer; the catalyst layer contains catalytic noble metals such as platinum (Pt), palladium (Pd), and rhodium (Rh). Consequently, when the exhaust gas passes through the catalyst layer, part of the hydrogen contained in the exhaust gas will be burnt due to catalysis by the catalytic noble metals. As a result, it is possible to suppress the output deviation of the gas sensor element due to the hydrogen contained in the exhaust gas.

On the other hand, the gas sensors are generally required to have quick responsiveness to change in the concentration of oxygen in the exhaust gas from the engine.

However, the components (e.g., $H_2$, CO, $O_2$) of the exhaust gas will cause oxidation and reduction reactions of the catalytic noble metals contained in the catalyst layer of the gas sensor element. Further, due to the oxidation and reduction reactions of the catalytic noble metals, the concentration of oxygen at the measurement electrode of the gas sensor element will change in proportion to the time and speed of the oxidation and reduction reactions. Consequently, a response delay of the gas sensor will occur due to the change in the concentration of oxygen at the measurement electrode.

The response delay of the gas sensor may be suppressed, in other words, quick responsiveness of the gas sensor may be secured by specifying the percentage contents of Pd and Rh in the catalyst layer of the gas sensor element within predetermined ranges as disclosed in Japanese Patent Application Publications No. 2007-199046 and No. 2010-276530.

However, by specifying the percentage contents of Pd and Rh in the catalyst layer as disclosed in the above two patent documents, it is possible to reliably secure quick responsiveness of the gas sensor only when the exhaust gas is changed from lean to rich. In other words, it may be difficult to reliably secure quick responsiveness of the gas sensor when the exhaust gas is changed from rich to lean only by specifying the percentage contents of Pd and Rh in the catalyst layer as disclosed in the above two patent documents.

SUMMARY

According to an exemplary embodiment, a gas sensor element is provided which includes a solid electrolyte body, a measurement electrode, a reference electrode, a porous diffusion-resistant layer and a catalyst layer. The solid electrolyte body has oxygen ion conductivity and an opposite pair of first and second surfaces. The measurement electrode is provided on the first surface of the solid electrolyte body so as to be exposed to a measurement gas. The reference electrode is provided on the second surface of the solid electrolyte body so as to be exposed to a reference gas. The diffusion-resistant layer is provided so that the measurement gas is introduced to the measurement electrode through the diffusion-resistant layer. The diffusion-resistant layer has an outer surface via which the measurement gas flows into the diffusion-resistant layer. The catalyst layer is formed on the outer surface of the diffusion-resistant layer and contains Pt, Pd and Rh. In the catalyst layer, the percentage content of Pt is in the range of 2.5 to 12 mass %, the percentage content of Pd is in the range of 0.4 to 2 mass %, and the percentage content of Rh is in the range of 0.06 to 1.5 mass %. The catalyst layer includes catalytic noble metal particles each of which is made of an alloy that contains at least Pt. Each of the catalytic noble metal particles has a core portion and an outer peripheral portion that surrounds the core portion. The percentage content of Pt at the outer peripheral portion is lower than that at the core portion.

With the above configuration, when the measurement gas passes through the catalyst layer, it is possible to burn a sufficient amount of hydrogen contained in the measurement gas, thereby reducing the amount of hydrogen reaching the measurement electrode. As a result, it is possible to suppress the output deviation of the gas sensor element due to the hydrogen contained in the measurement gas.

Further, by specifying the percentage contents of Pt, Pd and Rh in the catalyst layer to be respectively in the above ranges, it is possible to suppress a response delay of the gas sensor element both when the measurement gas is changed from lean to rich and when the measurement gas is changed from rich to lean.

More specifically, when the measurement gas is changed from lean to rich, a response delay of the gas sensor element may occur due to chemical reactions between the Rh contained in the catalyst layer and the components of the measurement gas. However, by specifying the percentage content of Rh in the catalyst layer to be in the range of 0.06 to 1.5 mass %, it is possible to suppress the response delay of the gas sensor element.

On the other hand, when the measurement gas is changed from rich to lean, a response delay of the gas sensor element may occur due to chemical reactions between the Pd contained in the catalyst layer and the components of the measurement gas. However, by specifying the percentage content of Pd in the catalyst layer to be in the range of 0.4 to 2 mass %, it is possible to suppress the response delay of the gas sensor element.

Moreover, Pt has superior catalytic performance. At the same time, the vapor pressure of Pt-oxide is high. Therefore, in a high-temperature atmosphere, Pt which is present on the outer surfaces of the catalytic noble metal particles of the catalyst layer may be dispersed by the phenomenon of transpiration. Consequently, it may become impossible to ensure durability of the catalytic noble metal particles.

However, in the above gas sensor element, with the lower percentage content of Pt at the outer peripheral portions of the catalytic noble metal particles, it is possible to suppress dispersion of Pt from the outer surfaces of the catalytic noble metal particles. Consequently, it is possible to suppress deterioration in the catalytic performance of the catalytic noble metal particles and secure high thermal durability of the catalytic noble metal particles. As a result, it is possible to maintain high output accuracy of the gas sensor element.

Furthermore, in the gas sensor element, the percentage contents of Pt, Pd and Rh in the catalyst layer are low as described above. The inventor of the present application has found that even with the low percentage contents of Pt, Pd and Rh in the catalyst layer, it is still possible to effectively suppress both a response delay and the output deviation of the gas sensor element by specifying the percentage contents of Pt, Pd and Rh to be respectively in the above ranges and setting the percentage content of Pt at the outer peripheral portions lower than that at the core portions of the catalytic noble metal particles. That is, it is possible to secure both quick responsiveness and high accuracy of the gas senor element while minimizing the manufacturing cost of the gas sensor element.

In addition, with the low percentage contents of Pt, Pd and Rh in the catalyst layer, the distances between the catalytic noble metal particles in the catalyst layer are accordingly increased. Consequently, it is possible to suppress aggregation of the catalytic noble metal particles in the catalyst layer, thereby ensuring stability of the catalytic noble metal particles and suppressing deterioration in the catalytic performance of the catalytic noble metal particles.

Preferably, each of the catalytic noble metal particles is made of one of a Pt—Pd alloy, a Pt—Rh alloy and a Pt—Pd—Rh alloy.

It is more preferable that each of the catalytic noble metal particles is made of a Pt—Pd—Rh alloy.

It is preferable that in the catalyst layer, the percentage content of Pt is in the range of 3 to 4.5 mass %, the percentage content of Pd is in the range of 0.8 to 1.2 mass %, and the percentage content of Rh is in the range of 0.2 to 0.3 mass %.

Preferably, for each of the catalytic noble metal particles, the percentage content of Pt at the core portion of the catalytic noble metal particle is higher than or equal to 50 mass %.

It is more preferable that the percentage content of Pt at the core portion of the catalytic noble metal particle is higher than or equal to 65 mass %.

Preferably, the gas sensor element further includes a porous protective layer that is formed at an outer periphery of the gas sensor element so as to cover at least the catalyst layer.

According to the exemplary embodiment, there is also provided a gas senor that includes the gas sensor element.

Since the gas sensor element has the above-described advantages, the gas sensor including the gas sensor element accordingly has both quick responsiveness and high accuracy.

BRIEF DESCRIPTION OF THE DRAWINGS

The present invention will be understood more fully from the detailed description given hereinafter and from the accompanying drawings of exemplary embodiments, which, however, should not be taken to limit the invention to the specific embodiments but are for the purpose of explanation and understanding only.

In the accompanying drawings.

DESCRIPTION OF EMBODIMENTS

Exemplary embodiments will be described hereinafter with reference to FIGS. 1-7. It should be noted that for the sake of clarity and understanding, identical components having identical functions in different embodiments have been marked, where possible, with the same reference numerals in each of the figures and that for the sake of avoiding redundancy, descriptions of the identical components will not be repeated.

[First Embodiment]

Figure 1:
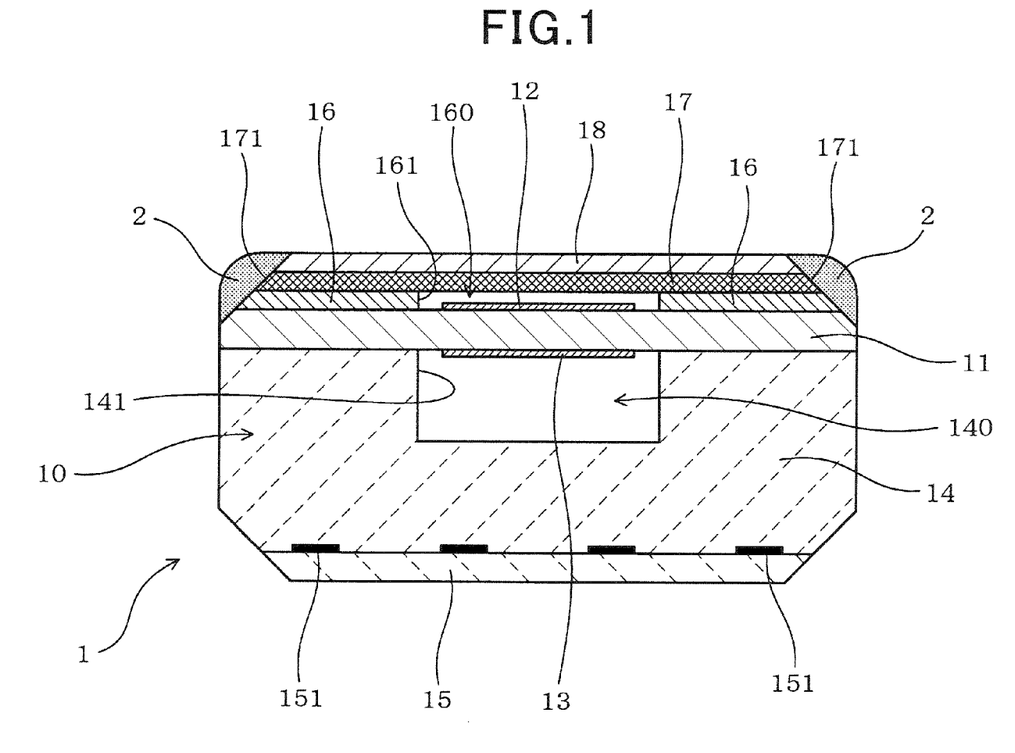
FIG. 1 is a cross-sectional view illustrating the overall configuration of a gas sensor element according to a first embodiment.

FIG. 1 shows the overall configuration of a gas sensor element 1 according to a first embodiment.

As shown in FIG. 1, the gas sensor element 1 includes a solid electrolyte body 11, a measurement electrode 12, a reference electrode 13, and a porous diffusion-resistant layer 17. The solid electrolyte body 11 has oxygen ion conductivity and an opposite pair of first and second surfaces (i.e., the upper and lower surfaces in FIG. 1). The measurement electrode 12 is provided on the first surface of the solid electrolyte body 11 so as to be exposed to a measurement gas. The reference electrode 13 is provided on the second surface of the solid electrolyte body 11 so as to be exposed to a reference gas. The porous diffusion-resistant layer 17 is provided on the same side of the solid electrolyte body 11 as the measurement electrode 12, so that the measurement gas is introduced to the measurement electrode 12 through the diffusion-resistant layer 17. In addition, the diffusion-resistant layer 17 is provided to limit the amount of the measurement gas introduced to the measurement electrode 12.

Figure 2:
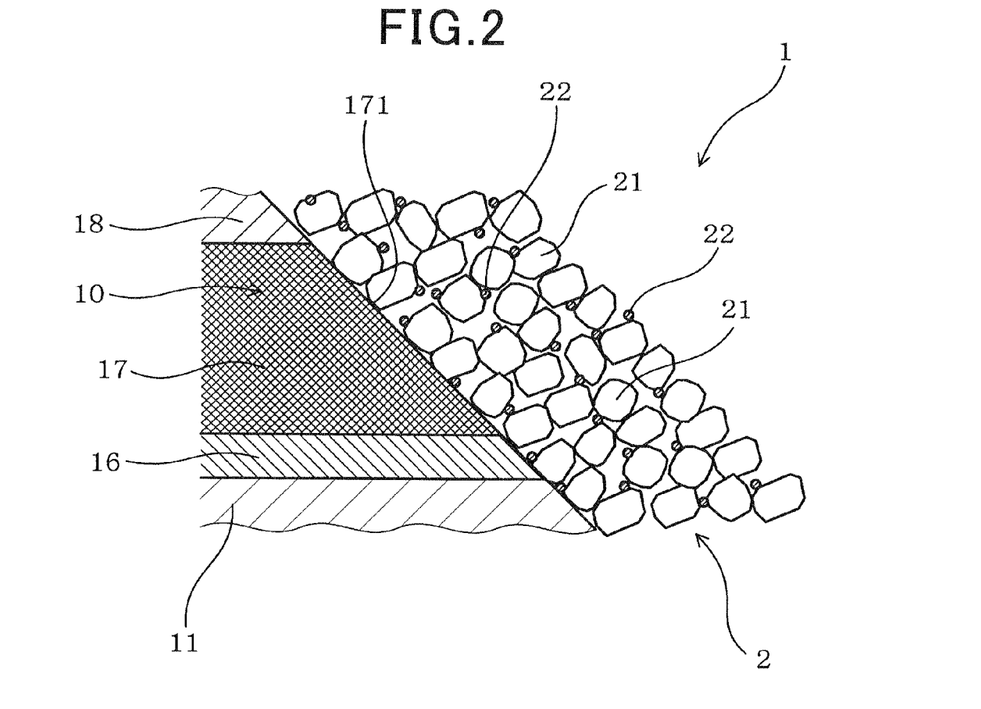
FIG. 2 is a schematic view illustrating the formation of a catalyst layer on an outer side surface of a porous diffusion-resistant layer in the gas sensor element.

Referring now to FIG. 2 together with FIG. 1, the gas sensor element 1 further includes a porous catalyst layer 2 that is formed on an outer side surface 171 of the diffusion-resistant layer 17. In addition, the measurement gas flows into the diffusion-resistant layer 17 via the outer side surface 171.

The catalyst layer 2 contains platinum (Pt), palladium (Pd) and rhodium (Rh), all of which are catalytic noble metals. Further, in the catalyst layer 2, the percentage content of Pt is in the range of 2.5 to 12 mass %, the percentage content of Pd is in the range of 0.4 to 2 mass %, and the percentage content of Rh is in the range of 0.06 to 1.5 mass %.

Figure 3:
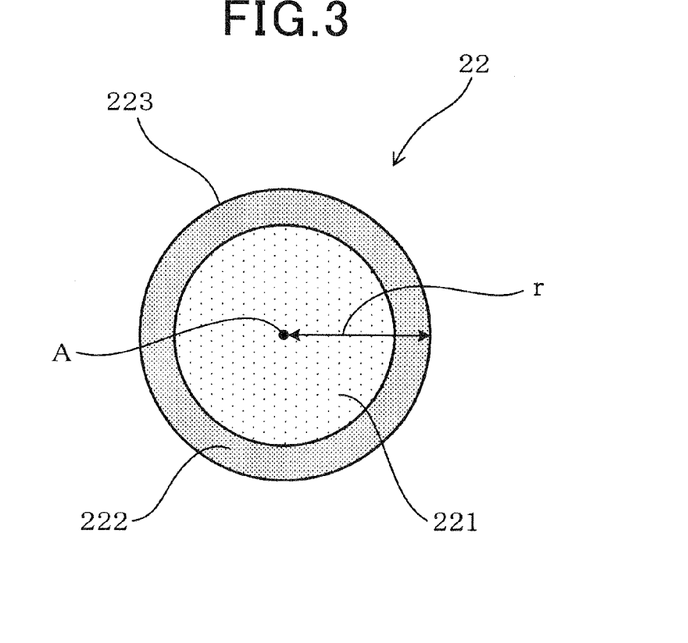
FIG. 3 is a schematic cross-sectional view illustrating a model of catalytic noble metal particles included in the catalyst layer.

The catalyst layer 2 includes catalytic noble metal particles 22 each of which is made of an alloy that contains at least Pt, such as a Pt—Pd alloy, a Pt—Rh alloy or a Pt—Pd—Rh alloy. Further, each of the catalytic noble metal particles 22 has a core portion 221 and an outer peripheral portion 222 that surrounds the core portion 221. The percentage content of Pt at the outer peripheral portion 222 is lower than that at the core portion 221.

The configuration of the gas sensor element 1 according to the present embodiment will be described in more detail hereinafter.

In the present embodiment, the gas sensor element 1 is configured as an A/F (Air/Fuel) ratio sensor element to sense the A/F ratio of air-fuel mixture supplied to an internal combustion engine of a motor vehicle. More specifically, in this case, the A/F ratio is determined based on the limit current of the gas sensor element 1 flowing between the measurement and reference electrodes 12 and 13; the limit current depends on the concentration of oxygen in the exhaust gas from the engine.

That is, in the present embodiment, the measurement gas is the exhaust gas from the engine, and the reference gas is air.

The gas sensor element 1 includes a main body 10 and the catalyst layer 2. The main body 10 includes the solid electrolyte body 11, the measurement and reference electrodes 12 and 13, the diffusion-resistant layer 17, a reference gas chamber formation layer 14, a heater substrate 15, an insulating layer 16 and a shield layer 18.

The solid electrolyte body 11 has oxygen ion conductivity and is made of, for example, zirconia.

The measurement and reference electrodes 12 and 13 are respectively provided on the first and second surfaces of the solid electrolyte body 11. Both the measurement and reference electrodes 12 and 13 are made of, for example, Pt.

The reference gas chamber formation layer 14 is laminated on the second surface of the solid electrolyte body 11 around the reference electrode 13. The reference gas chamber formation layer 14 is made of, for example, dense alumina that is gas impermeable and electrically insulative. In that surface of the reference gas chamber formation layer 14 which abuts the second surface of the solid electrolyte body 11, there is formed a groove 141 that makes up a reference gas chamber 140. The reference electrode 13 is located within the reference gas chamber 140. In operation, the reference gas chamber 140 is filled with the reference gas which is introduced into the chamber 140 via an opening (not shown) of the chamber 140; consequently, the reference electrode 13 is exposed to the reference gas.

On that surface of the reference gas chamber formation layer 14 which is on the opposite side to the solid electrolyte body 11, there is laminated the heater substrate 15. An electrical heating element 151 is provided in the heater substrate 15 so as to face the reference gas chamber formation layer 14. In operation, the heating element 151 is supplied with electric power to generate heat, thereby heating the gas sensor element 1 to an activation temperature of the solid electrolyte layer 11.

The insulating layer 16 is laminated on the first surface of the solid electrolyte body 11 around the measurement electrode 12. The insulating layer 16 is made of, for example, dense alumina that is gas impermeable and electrically insulative. The insulating layer 16 has formed therein an opening 161 that makes up a measurement gas chamber 160. The measurement electrode 12 is located within the measurement gas chamber 160.

On that surface of the insulating layer 16 which is on the opposite side to the solid electrolyte body 11, there is laminated the diffusion-resistant layer 17 so as to face the measurement gas chamber 160. The diffusion-resistant layer 17 is made of, for example, gas-permeable porous alumina In operation, the measurement gas chamber 160 is filled with the measurement gas which is introduced into the chamber 160 via the diffusion-resistant layer 17; consequently, the measurement electrode 12 is exposed to the measurement gas.

The shield layer 18 is laminated on that surface of the diffusion-resistant layer 17 which is on the opposite side to the insulating layer 16. The shield layer 18 is made of, for example, dense alumina that is gas impermeable and electrically insulative.

In addition, the outer side surface 171 of the diffusion-resistant layer 17 is exposed from the shield layer 18, so as to make up a measurement gas inlet. In operation, the measurement gas is first introduced into the diffusion-resistant layer 17 via the measurement gas inlet 171 and then flows, through the inside of the diffusion-resistant layer 17, into the measurement gas chamber 160 in which the measurement electrode 12 is received.

The porous catalyst layer 2 is formed on the outer side surface 171 of the diffusion-resistant layer 17 so that the measurement gas is introduced to the diffusion-resistant layer 17 through the catalyst layer 2.

The catalyst layer 2 contains Pt, Pd and Rh so that in the catalyst layer 2, the percentage content of Pt is in the range of 2.5 to 12 mass %, the percentage content of Pd is in the range of 0.4 to 2 mass %, and the percentage content of Rh is in the range of 0.06 to 1.5 mass %.

In addition, the percentage content of each of the noble metal elements Pt, Pd and Rh represents the ratio of the mass of the noble metal element contained in the catalyst layer 2 to the total mass of the catalyst layer 2. The percentage contents of the noble metal elements in the catalyst layer 2 may be determined by a quantitative analysis using, for example, an Electron Micro Probe Analyzer (EPMA) or a Transmission Electron Microscope (TEM).

Moreover, in the present embodiment, the catalyst layer 2 is formed of a mixture of supporting particles 21, the catalytic noble metal particles 22, and glass particles (not shown in FIG. 2).

The supporting particles 21 are made of alumina, more specifically α-alumina, β-alumina, or γ-alumina. The catalytic noble metal particles 22 are supported by the supporting particles 21. Each of the catalytic noble metal particles 22 is made of an alloy that contains at least Pt, such as a Pt—Pd alloy, a Pt—Rh alloy or a Pt—Pd—Rh alloy. More specifically, in the present embodiment, all the catalytic noble metal particles 22 are essentially made of a Pt—Pd—Rh alloy.

Further, referring to FIG. 3, for each of the catalytic noble metal particles 22, the percentage content of Pt at the outer peripheral portion 222 of the catalytic noble metal particle 22 is lower than that at the core portion 221 of the catalytic noble metal particle 22.

Furthermore, in the present embodiment, for each of the catalytic noble metal particles 22, the percentage content of Pt at the core portion 221 of the catalytic noble metal particle 22 is higher than or equal to 50 mass %.

Moreover, as shown in FIG. 3, for each of the catalytic noble metal particles 22, the outer peripheral portion 222 denotes that portion of the catalytic noble metal particle 22 which extends from the outer surface 223 of the catalytic noble metal particle 22 radially inward (or toward the center A of the catalytic noble metal particle 22) by a predetermined distance, more specifically by ¼ of an average particle radius r of the catalytic noble metal particles 22 in the present embodiment. The core portion 221 denotes the remaining portion of the catalytic noble metal particle 22.

In addition, the average particle radius r of the catalytic noble metal particles 22 may be determined by: (1) observing and photoing a field of view that includes the catalytic noble metal particles 22 using, for example, a Field Emission-Scanning Electron Microscope (FE-SEM) at a predetermined magnification; and (2) taking the arithmetic mean of radii of a given number (e.g., 10 or more) of the catalytic noble metal particles 22. Moreover, for each of the catalytic noble metal particles 22, the percentage contents of Pt at the core portion 221 and outer peripheral portion 222 of the catalytic noble metal particle 22 may be determined by a quantitative analysis using, for example, a TEM.

After having described the configuration of the gas sensor element 1, a method of manufacturing it according to the present embodiment will be described hereinafter.

In the present embodiment, the method of manufacturing the gas sensor element 1 includes a preparing step, an application step and a heat treatment step.

In the preparing step, the main body 10 and a paste for forming the catalyst layer 2 are prepared.

More specifically, in this step, ceramic sheets for respectively forming the heater substrate 15, the reference gas chamber formation layer 14, the solid electrolyte body 11, the insulating layer 16, the diffusion-resistant layer 17 and the shield layer 18 are sequentially laminated to form a laminate. Then, the laminate is fired at 1400 to 1500° C. for one to three hours, thereby forming the main body 10.

Further, in this step, the alumina particles 21, the catalytic noble metal particles 22, the glass particles, an organic solvent (e.g., terpineol) and an organic binder (e.g., ethyl cellulose) are mixed and kneaded, thereby obtaining the paste for forming the catalyst layer 2.

In addition, the catalytic noble metal particles 22 are obtained by: (1) mixing an acid solution that contains ions of Pt, Pd and Rh; and (2) causing reduction reactions of those ions in the acid solution using a reducing agent, thereby depositing Pt—Pd—Rh alloy particles. It should be noted that by controlling the speed of the reduction reactions and the depositing speed, each of the Pt—Pd—Rh alloy particles is deposited with Pd, Pt and Rh sequentially arranged from the center to the outer periphery of the particle.

In the application step, the paste for forming the catalyst layer 2 is applied on the outer side surface 171 of the diffusion-resistant layer 17 of the main body 10 by, for example, pad printing or screen printing.

In the heat treatment step, the main body 10, which has the paste for forming the catalyst layer 2 applied thereon, is first heated at 100 to 160° C. for 1 to 20 minutes and then further heated at 800 to 950° C. for one hour. Consequently, the paste is dried and fired, thereby forming the catalyst layer 2.

In addition, in this step, in each of the catalytic noble metal particles 22 (i.e., the Pt—Pd—Rh alloy particles), Pt, which has a high specific gravity, is moved inward so that the percentage content of Pt at the core portion 221 becomes higher than that at the outer peripheral portion 222.

As a result, the gas sensor element 1 according to the present embodiment is obtained.

Figure 4:
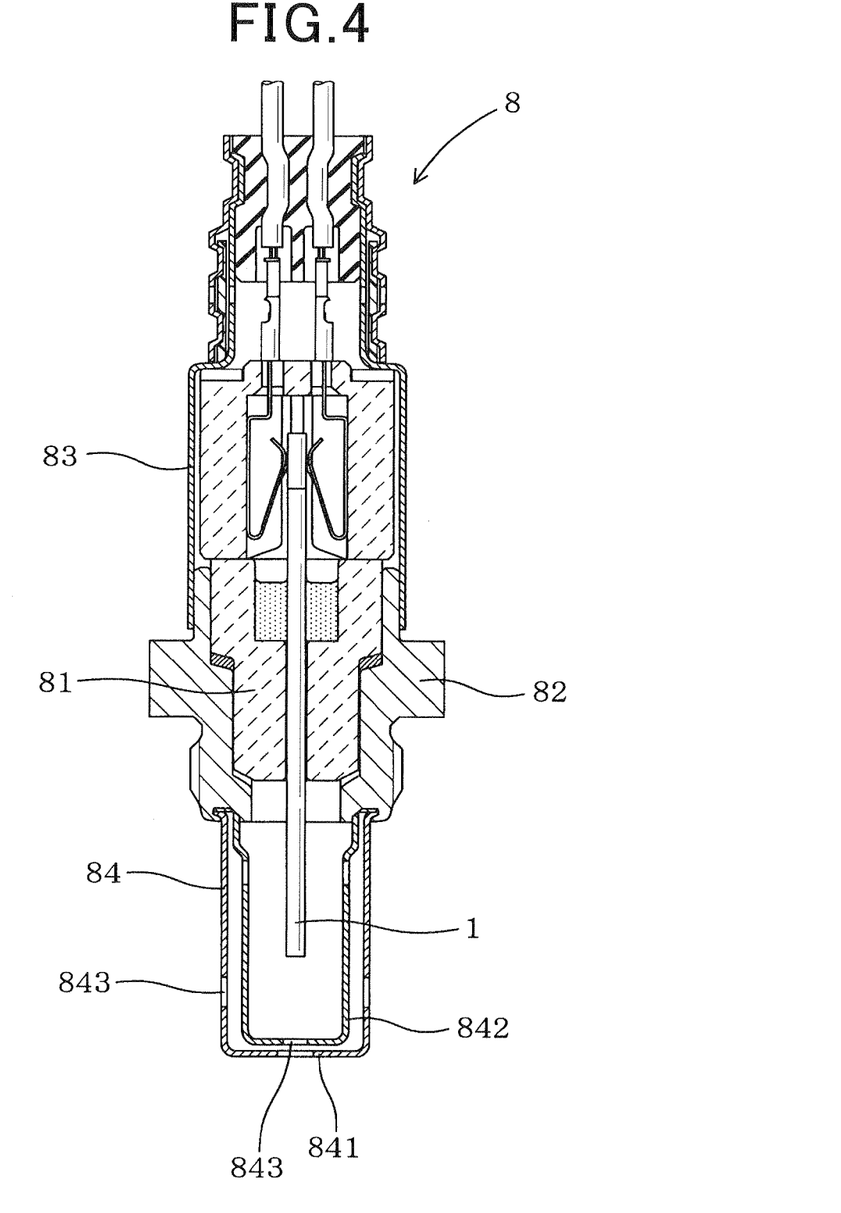
FIG. 4 is a cross-sectional view of a gas sensor that includes the gas sensor element according to the first embodiment.

Next, a gas sensor 8 which has the gas sensor element 1 incorporated therein will be described with reference to FIG. 4.

The gas sensor 8 includes, in addition to the gas sensor element 1, an insulator 81, a housing 82, a base-side cover 83 and a tip-side cover 84. The insulator 81 has the gas sensor element 1 partially inserted and held therein. The housing 82 has the insulator 81 partially inserted and held therein. The base-side cover 83 is fixed to a base end (i.e., the upper end in FIG. 4) of the housing 82 to protect that part of the insulator 81 which protrudes from the base end of the housing 81. The tip-side cover 84 is fixed to a tip end (i.e., the lower end in FIG. 4) of the housing 82 to protect that part of the gas sensor element 1 which protrudes from the tip end of the housing 82. The tip-side cover 84 is a double cover consisting of an outer cover 841 and an inner cover 842. Each of the inner and outer covers 841 and 842 has through-holes 843 formed through its end and side walls. In operation of the gas sensor 8, the measurement gas is introduced to the gas sensor element 1 through the through-holes 843 of the inner and outer covers 841 and 842.

According to the present embodiment, it is possible to achieve the following advantages.

As described above, in the present embodiment, the gas sensor element 1 has the catalyst layer 2 formed on the outer side surface 171 of the diffusion-resistant layer 17. The catalyst layer 2 contains Pt, Pd and Rh, all of which are catalytic noble metals.

Consequently, when the exhaust gas from the engine (i.e., the measurement gas) passes through the catalyst layer 2, it is possible to burn a sufficient amount of the hydrogen contained in the exhaust gas, thereby reducing the amount of the hydrogen reaching the measurement electrode 12. As a result, it is possible to suppress the output deviation of the gas sensor element 1 due to the hydrogen contained in the exhaust gas.

Further, in the present embodiment, in the catalyst layer 2, the percentage content of Pt is in the range of 2.5 to 12 mass %, the percentage content of Pd is in the range of 0.4 to 2 mass %, and the percentage content of Rh is in the range of 0.06 to 1.5 mass %.

By specifying the percentage contents of Pt, Pd and Rh in the catalyst layer 2 to be respectively in the above ranges, it is possible to suppress a response delay of the gas sensor element 1 both when the exhaust gas is changed from lean to rich and when the exhaust gas is changed from rich to lean.

More specifically, when the exhaust gas is changed from lean to rich, a response delay of the gas sensor element 1 may occur due to chemical reactions between the Rh contained in the catalyst layer 2 and the components of the exhaust gas.

However, by specifying the percentage content of Rh in the catalyst layer 2 to be in the range of 0.06 to 1.5 mass %, it is possible to suppress the response delay of the gas sensor element 1.

On the other hand, when the exhaust gas is changed from rich to lean, a response delay of the gas sensor element 1 may occur due to chemical reactions between the Pd contained in the catalyst layer 2 and the components of the exhaust gas. However, by specifying the percentage content of Pd in the catalyst layer 2 to be in the range of 0.4 to 2 mass %, it is possible to suppress the response delay of the gas sensor element 1.

Moreover, in the present embodiment, the catalyst layer 2 includes the catalytic noble metal particles 22 each of which is made of an alloy that contains at least Pt, more specifically a Pt—Pd—Rh alloy. For each of the catalytic noble metal particles 22, the percentage content of Pt at the outer peripheral portion 222 of the catalytic noble metal particle 22 is lower than that at the core portion 221 of the catalytic noble metal particle 22. In other words, the percentage content of Pt at the core portion 221 is higher than that at the outer peripheral portion 222.

In general, Pt has superior catalytic performance. At the same time, the vapor pressure of Pt-oxide is high. Therefore, in a high-temperature atmosphere, Pt which is present on the outer surfaces 223 of the catalytic noble metal particles 22 may be dispersed by the phenomenon of transpiration. Consequently, it may become impossible to ensure durability of the catalytic noble metal particles 22.

However, in the present embodiment, with the lower percentage content of Pt at the outer peripheral portions 222 of the catalytic noble metal particles 22, it is possible to suppress dispersion of Pt from the outer surfaces 223 of the catalytic noble metal particles 22. Consequently, it is possible to suppress deterioration in the catalytic performance of the catalytic noble metal particles 22 and secure high thermal durability of the catalytic noble metal particles 22. As a result, it is possible to maintain high output accuracy of the gas sensor element 1.

Furthermore, in the present embodiment, the percentage contents of Pt, Pd and Rh in the catalyst layer 2 are low as described above. The inventor of the present application has found that even with the low percentage contents of Pt, Pd and Rh in the catalyst layer 2, it is still possible to effectively suppress both a response delay and the output deviation of the gas sensor element 1 by specifying the percentage contents of Pt, Pd and Rh to be respectively in the above-described ranges and setting the percentage content of Pt at the outer peripheral portions 222 lower than that at the core portions 221 of the catalytic noble metal particles 22. That is, it is possible to secure both quick responsiveness and high accuracy of the gas senor element 1 while minimizing the manufacturing cost of the gas sensor element 1.

In addition, with the low percentage contents of Pt, Pd and Rh in the catalyst layer 2, the distances between the catalytic noble metal particles 22 in the catalyst layer 2 are accordingly increased. Consequently, it is possible to suppress aggregation of the catalytic noble metal particles 22 in the catalyst layer 2, thereby ensuring stability of the catalytic noble metal particles 22 and suppressing deterioration in the catalytic performance of the catalytic noble metal particles 22.

In the present embodiment, each of the catalytic noble metal particles 22 is made of the Pt—Pd—Rh alloy.

Among the three catalytic noble metals Pt, Pd and Rh, Pd has a stable catalytic performance even in an oxidizing atmosphere. Rh has a relatively high melting point and is thus superior in heat resistance. With Pt, it is possible to suppress aggregation of the catalytic noble metal particles 22 in a reducing atmosphere. Therefore, by forming each of the catalytic noble metal particles 22 with the Pt—Pd—Rh alloy, it is possible to suppress deterioration in the catalytic performance of the catalytic noble metal particles 22 in any of an oxidizing atmosphere, a reducing atmosphere and a high-temperature atmosphere.

In the present embodiment, for each of the catalytic noble metal particles 22, the percentage content of Pt at the core portion 221 of the catalytic noble metal particle 22 is higher than or equal to 50 mass %. Consequently, it is possible to more effectively suppress deterioration in the catalytic performance of the catalytic noble metal particles 22.

In the present embodiment, the gas sensor 8 includes the gas sensor element 1 having the above-described advantages. Accordingly, the gas sensor 8 has both quick responsiveness and high accuracy.

In addition, it is preferable that in the catalyst layer 2, the percentage content of Pt is in the range of 3 to 4.5 mass %, the percentage content of Pd is in the range of 0.8 to 1.2 mass %, and the percentage content of Rh is in the range of 0.2 to 0.3 mass %. In this case, it is possible to further improve the effect of suppressing both a response delay and the output deviation of the gas sensor element 1.

It is also preferable that for each of the catalytic noble metal particles 22, the percentage content of Pt at the core portion 221 of the catalytic noble metal particle 22 is higher than or equal to 65 mass %. In this case, it is possible to further improve the effect of suppressing deterioration in the catalytic performance of the catalytic noble metal particles 22.

[Experiment]

This experiment has been conducted to investigate the performance of the gas sensor element 1 according to the first embodiment.

In the experiment, gas sensor element samples A1-A21 were tested and evaluated in terms of responsiveness and accuracy at 700 to 800° C.

Figure 5:
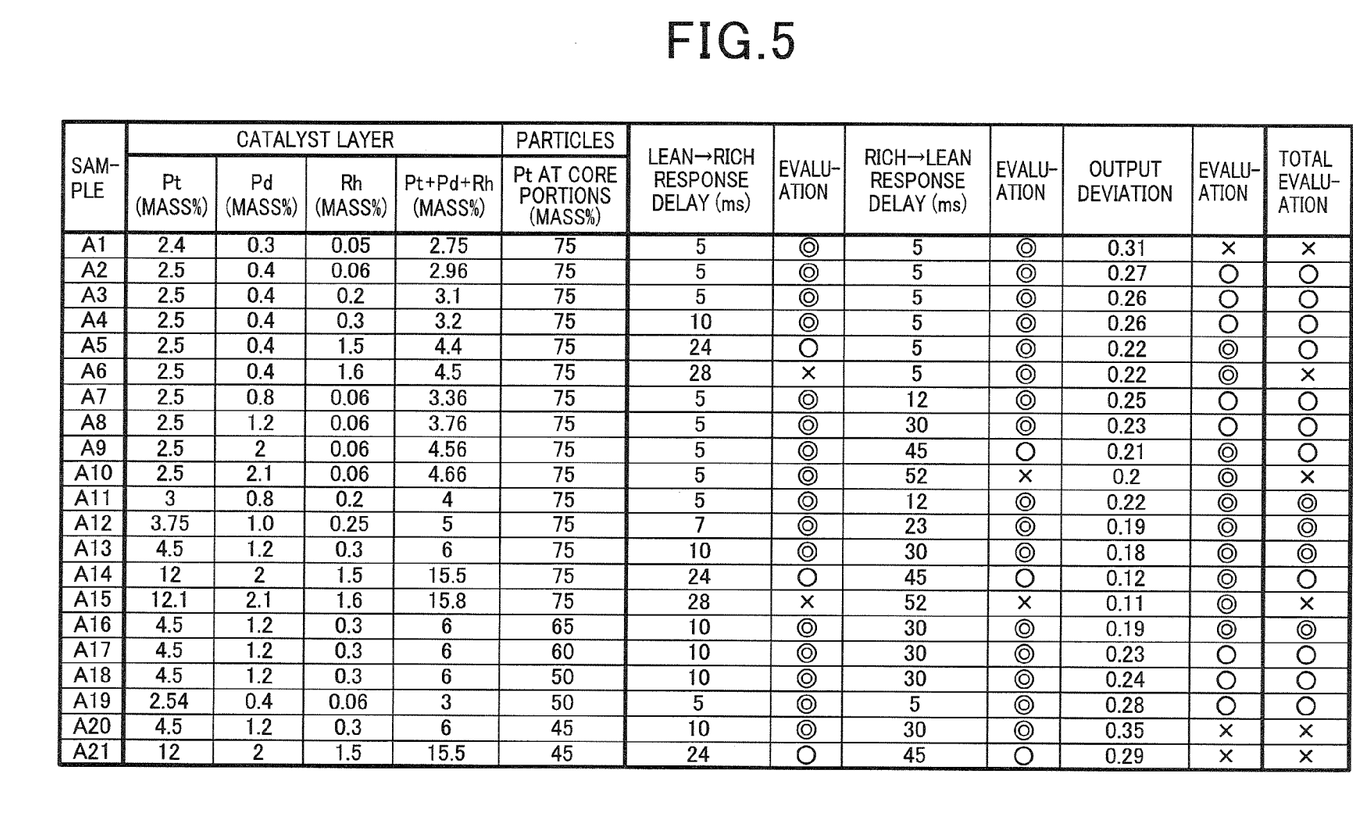
FIG. 5 is a tabular representation showing the results of an experiment for investigating the performance of the gas sensor element according to the first embodiment.

Each of the samples A1-A21 had the same configuration as the gas sensor element 1 according to the first embodiment (see FIGS. 1-2). However, as shown in FIG. 5, the percentage contents of Pt, Pd and Rh in the catalyst layer 2 and the percentage content of Pt at the core portions 221 of the catalytic noble metal particles 22 of the catalyst layer 2 were varied for the samples A1-A21.

For each of the samples A1-A21, the percentage contents of Pt, Pd and Rh in the catalyst layer 2 were determined by a quantitative analysis using an EPMA. On the other hand, the percentage content of Pt at the core portions 221 of the catalytic noble metal particles 22 of the catalyst layer 2 was determined by a quantitative analysis using a TEM. In addition, prior to the quantitative analysis using the TEM, the surfaces of the samples A1-A21 were processed using a Focused Ion Beam (FIB) processing device. Moreover, the percentage content of Pt at the outer peripheral portions 222 of the catalytic noble metal particles 22 was also determined; the determined percentage content of Pt at the outer peripheral portions 222 was lower than that at the core portions 221 of the catalytic noble metal particles 22.

First, each of the samples A1-A21 was tested and evaluated in terms of responsiveness.

Specifically, for each of the samples A1-A21, a gas sensor which had the sample built therein was connected to a gas generator so as to be exposed to a test gas generated by the gas generator. Then, the concentrations of $H_2$, CO and $O_2$ contained in the test gas were gradually changed, thereby changing the test gas from lean to rich and from rich to lean. The change in the test gas causes the output of the gas sensor to change, and the change in the output of the gas sensor was monitored. Thereafter, a response delay of the sample was determined as the length of the time period from when the concentrations of the components of the test gas were changed until the output of the gas sensor was changed due to the change in the test gas. In addition, the above determination of the response delay was made after exposing the gas sensor to the test gas the atmosphere of which was rich (the A/F ratio was equal to 13).

Further, the responsiveness of the sample to the change in the test gas from lean to rich was evaluated: (1) as being very good and denoted by "⊚" in FIG. 5 when the response delay was not longer 10 ms; (2) as being good and denoted by "○" in FIG. 5 when the response delay was longer than 10 ms but not longer than 25 ms; and (3) as being "bad" and denoted by "x" in FIG. 5 when the response delay was longer than 25 ms.

On the other hand, the responsiveness of the sample to the change in the test gas from rich to lean was evaluated: (1) as being very good and denoted by "⊚" in FIG. 5 when the response delay was not longer 30 ms; (2) as being good and denoted by "○" in FIG. 5 when the response delay was longer than 30 ms but not longer than 50 ms; and (3) as being "bad" and denoted by "x" in FIG. 5 when the response delay was longer than 50 ms.

Next, each of the samples A1-A21 was tested and evaluated in terms of accuracy.

Specifically, for each of the samples A1-A21, a gas sensor which had the sample built therein was subjected to an endurance test in which the catalyst layer 2 of the sample was exposed to an air atmosphere of 900° C. for 200 hours. Then, the gas sensor was exposed to a test gas of a stoichiometric atmosphere (the A/F ratio was equal to 14.5). The test gas contained $H_2$, CO and $O_2$, and the percentage content of $H_2$ in the test gas was 0.5 mass %. Thereafter, the output of the gas sensor was measured, and the A/F ratio of the test gas was determined based on the measured output of the gas sensor. The difference between the determined A/F ratio and the actual A/F ratio (i.e., 14.5) was employed to represent the output deviation of the sample.

Further, the accuracy of the sample was evaluated: (1) as being very good and denoted by "⊚" in FIG. 5 when the output deviation of the sample was not greater than 0.22; (2) as being good and denoted by "○" in FIG. 5 when the output deviation of the sample was greater than 0.22 but not greater than 0.28; and (3) as being "bad" and denoted by "x" in FIG. 5 when the output deviation of the sample was greater than 0.28.

Finally, a total evaluation was made for each of the samples A1-A21. Specifically, each of the samples A1-A21 was evaluated: (1) as being very good and denoted by "⊚" in FIG. 5 when all of the three parameters, i.e., the responsiveness of the sample to the change in the test gas from lean to rich, the responsiveness of the sample to the change in the test gas from rich to lean and the accuracy of the sample had been evaluated as being very good; (2) as being good and denoted by "○" in FIG. 5 when none of the three parameters had been evaluated as being bad but at least one of the three parameters had been evaluated as only good; and (3) as being "bad" and denoted by "x" in FIG. 5 when at least one of the three parameters had been evaluated as being bad.

As shown in FIG. 5, among all the samples A1-A21, the samples A2-A5, A7-A9, A11-A14 and A16-A19 were evaluated as being good or very good. In each of the samples A2-A5, A7-A9, A11-A14 and A16-A19, the percentage contents of Pt, Pd and Rh in the catalyst layer 2 were respectively in the range of 2.5 to 12 mass %, in the range of 0.4 to 2 mass % and in the range of 0.06 to 1.5 mass %; the percentage content of Pt at the core portions 221 of the catalytic noble metal particles 22 of the catalyst layer 2 was higher than or equal to 50%.

In particular, the samples A11-A13 and A16 were evaluated as being very good. In each of the samples A11-A13 and A16, the percentage contents of Pt, Pd and Rh in the catalyst layer 2 were respectively in the range of 3 to 4.5 mass %, in the range of 0.8 to 1.2 mass % and in the range of 0.2 to 0.3 mass %; the percentage content of Pt at the core portions 221 of the catalytic noble metal particles 22 of the catalyst layer 2 was higher than or equal to 65%.

In contrast, the samples A1, A6, A10, A15 and A20-A21 were evaluated as being bad. In each of the samples A1, A6, A10 and A15, at least one of the percentage contents of Pt, Pd and Rh in the catalyst layer 2 was out of the above-described ranges, i.e., the range of 2.5 to 12 mass % for Pt, the range of 0.4 to 2 mass % for Pd and the range of 0.06 to 1.5 mass % for Rh. On the other hand, in each of the samples A20-A21, the percentage content of Pt at the core portions 221 of the catalytic noble metal particles 22 of the catalyst layer 2 was lower than 50%. In addition, each of the samples A20-A21 was evaluated as being bad due to the accuracy thereof evaluated as being bad.

Accordingly, from the above experimental results, it is made clear that:
- by specifying the percentage contents of Pt, Pd and Rh in the catalyst layer 2 to be respectively in the range of 2.5 to 12 mass %, in the range of 0.4 to 2 mass % and in the range of 0.06 to 1.5 mass %, it is possible to secure both quick responsiveness and high accuracy of the gas senor element 1;
- by specifying the percentage contents of Pt, Pd and Rh in the catalyst layer 2 to be respectively in the range of 3 to 4.5 mass %, in the range of 0.8 to 1.2 mass % and in the range of 0.2 to 0.3 mass %, it is possible to more reliably secure both quick responsiveness and high accuracy of the gas senor element 1;
- by specifying the percentage content of Pt at the core portions 221 of the catalytic noble metal particles 22 of the catalyst layer 2 to be higher than or equal to 50%, it is possible to effectively suppress deterioration in the catalytic performance of the catalytic noble metal particles 22, thereby reliably maintaining the accuracy of the gas senor element 1; and
- by specifying the percentage content of Pt at the core portions 221 of the catalytic noble metal particles 22 to be higher than or equal to 65%, it is possible to more effectively suppress deterioration in the catalytic performance of the catalytic noble metal particles 22, thereby more reliably maintaining the accuracy of the gas senor element 1.

[Second Embodiment]

This embodiment illustrates a gas sensor element 1 which has a similar configuration to the gas sensor element 1 according to the first embodiment; accordingly, only the differences therebetween will be described hereinafter.

In the first embodiment, the catalyst layer 2 is directly exposed to the outside of the gas sensor element 1 without any other member covering it (see FIG. 1).

Figure 6:
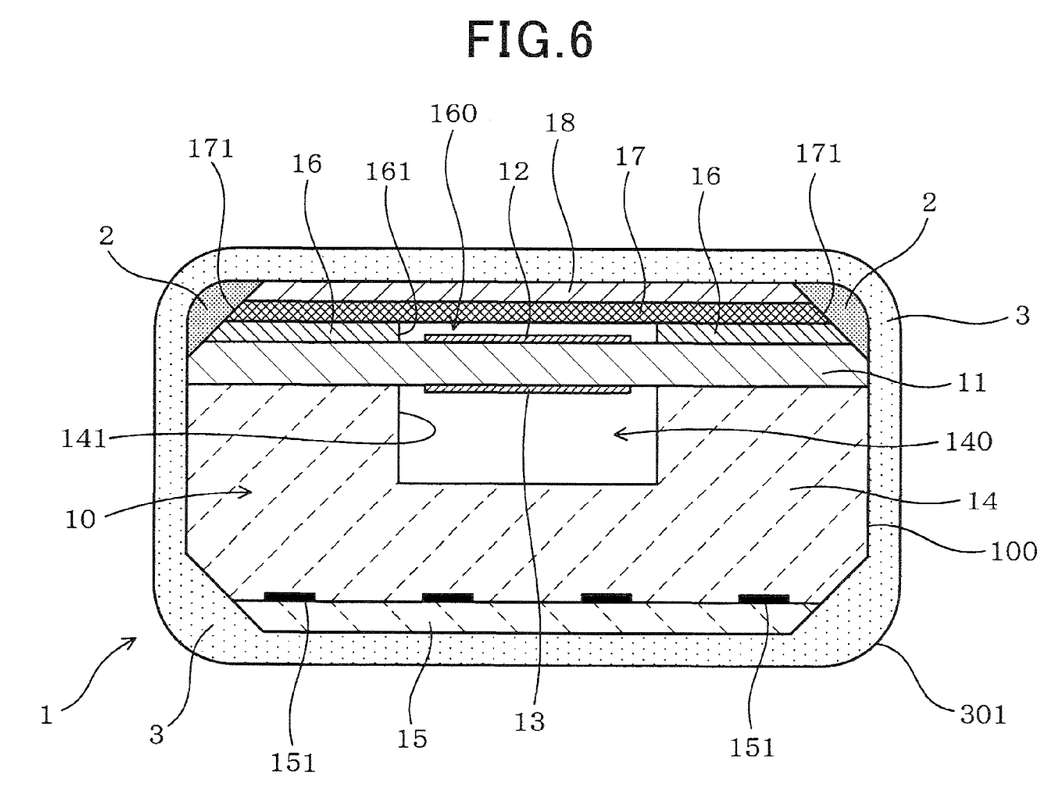
FIG. 6 is a cross-sectional view illustrating the overall configuration of a gas sensor element according to a second embodiment.

In comparison, in the present embodiment, as shown in FIG. 6, the gas sensor element 1 further includes a porous protective layer 3 that is formed at the outer periphery of the gas sensor element 1 so as to completely cover both the catalyst layer 2 and the outer surface 100 of the main body 10 of the gas sensor element 1 exposed from the catalyst layer 2. Consequently, the measurement gas is introduced to the catalyst layer 2 through the protective layer 3.

The protective layer 3 is made of alumina-based ceramic particles. The porosity of the protective layer 3 is about 60%. The outer surface 301 of the protective layer 3 is directly exposed to the outside of the gas sensor element 1.

The gas sensor element 1 according to the present embodiment has the same advantages as that according to the first embodiment.

In addition, in the present embodiment, with the protective layer 3, it is possible to reliably prevent the main body 10 of the gas sensor element 1 from being damaged by water included in the measurement gas during operation.

[Third Embodiment]

This embodiment illustrates a gas sensor element 1 which has a similar configuration to the gas sensor element 1 according to the first embodiment; accordingly, only the differences therebetween will be described hereinafter.

Figure 7:
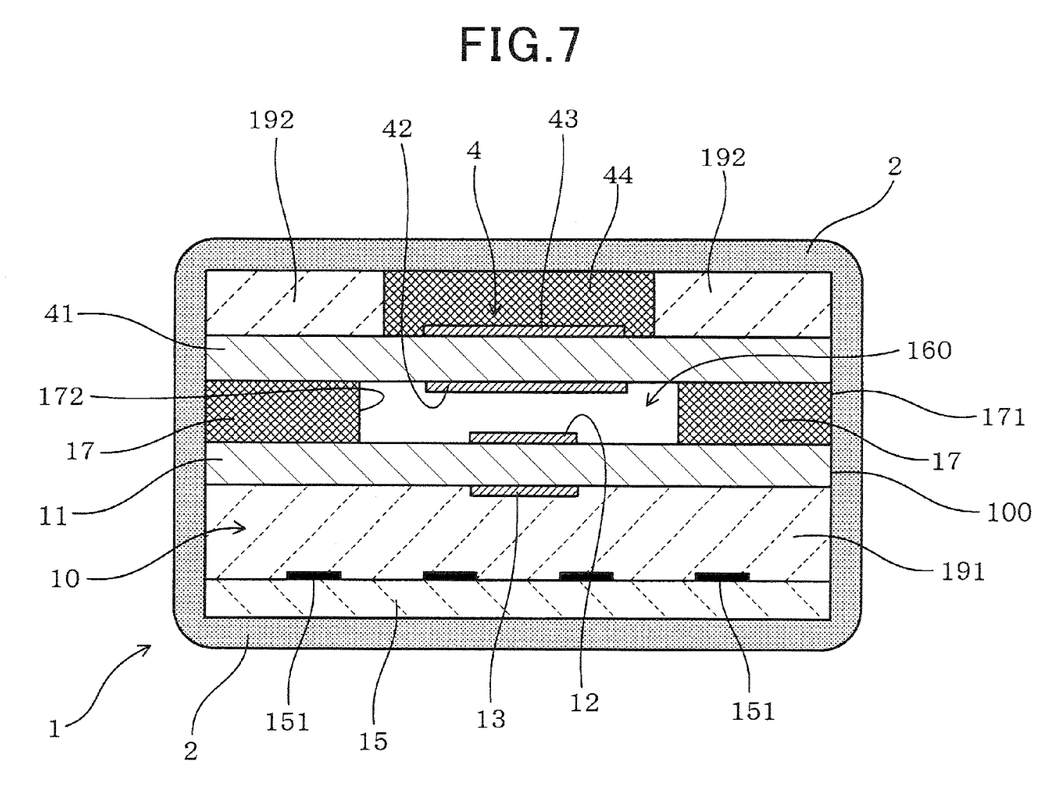
FIG. 7 is a cross-sectional view illustrating the overall configuration of a gas sensor element according to a third embodiment.

As shown in FIG. 7, in the present embodiment, the main body 10 of the gas sensor element 1 includes the solid electrolyte body 11, the measurement electrode 12, the reference electrode 13, the heater substrate 15 and the diffusion-resistant layer 17 as in the first embodiment. However, the reference gas chamber formation layer 14, the insulating layer 16 and the shield layer 18 are omitted from the main body 10. Instead, the main body 10 further includes an insulating layer 191, a pump cell 4, a porous diffusion-resistant layer 44 and an insulating layer 192.

More specifically, in the present embodiment, the diffusion-resistant layer 17 is laminated directly on the first surface (i.e., the upper surface in FIG. 7) of the solid electrolyte body 11 around the measurement electrode 12. The diffusion-resistant layer 17 has formed therein an opening 172 that makes up the measurement gas chamber 160, within which the measurement electrode 12 is located.

On the second surface (i.e., the lower surface in FIG. 7) of the solid electrolyte body 11, there is laminated the insulating layer 191 so as to cover the reference electrode 13. On that surface of the insulating layer 191 which is on the opposite side to the solid electrolyte body 11, there is laminated the heater substrate 15. The electrical heating element 151 is provided in the heater substrate 15 so as to face the insulating layer 191.

The pump cell 4 is provided to adjust the concentration of oxygen in the measurement gas chamber 160. The pump cell 4 is comprised of a solid electrolyte body 41 and a pair of electrodes 42 and 43. The solid electrolyte body 41 has oxygen ion conductivity and is laminated on that surface of the diffusion-resistant layer 17 which is on the opposite side to the solid electrolyte body 11. The electrode 42 is provided on one surface (i.e., the lower surface in FIG. 7) of the solid electrolyte body 41 to face the measurement gas chamber 160. The electrode 43 is provided on the other surface (i.e., the upper surface in FIG. 7) of the solid electrolyte body 41.

The diffusion-resistant layer 44 is provided on the other surface of the solid electrolyte body 41 so as to cover the electrode 43 of the pump cell 4.

The insulating layer 192 is also provided on the other surface of the solid electrolyte body 41 around the diffusion-resistant layer 44.

In the present embodiment, the catalyst layer 2 is formed so as to cover the entire outer surface 100 of the main body 10 which includes the outer side surface 171 of the diffusion-resistant layer 17.

The above-described gas sensor element 1 according to the present embodiment has the same advantages as that according to the first embodiment.

While the above particular embodiments have been shown and described, it will be understood by those skilled in the art that various modifications, changes, and improvements may be made without departing from the spirit of the invention.

For example, in the first embodiment, the gas sensor element 1 is configured as an A/F ratio sensor element to sense the A/F ratio of air-fuel mixture supplied to an internal combustion engine of a motor vehicle.

However, the gas sensor element 1 may also be configured as an oxygen sensor element to sense the concentration of oxygen in the exhaust gas from an internal combustion engine of a motor vehicle. More specifically, in this case, the concentration of oxygen in the exhaust gas may be determined based on the electromotive force created between the measurement and reference electrodes 12 and 13; the electromotive force depends on the ratio between the concentration of oxygen in the measurement gas (i.e., the exhaust gas) and the concentration of oxygen in the reference gas (i.e., air).

In the first embodiment, the gas sensor element 1 is a laminated sensor element in which are laminated the heater substrate 15, the reference gas chamber formation layer 14, the solid electrolyte body 11, the insulating layer 16, the diffusion-resistant layer 17 and the shield layer 18.

However, the invention can also be applied to a cup-shaped gas sensor element which includes a solid electrolyte body having both a closed tip end and an open base end.

What is claimed is:

1. A gas sensor element comprising:
   a solid electrolyte body having oxygen ion conductivity and an opposite pair of first and second surfaces;
   a measurement electrode provided on the first surface of the solid electrolyte body so as to be exposed to a measurement gas;
   a reference electrode provided on the second surface of the solid electrolyte body so as to be exposed to a reference gas;
   a porous diffusion-resistant layer through which the measurement gas is introduced to the measurement electrode, the diffusion-resistant layer having an outer surface via which the measurement gas flows into the diffusion-resistant layer; and
   a catalyst layer that is formed on the outer surface of the diffusion-resistant layer and contains Pt, Pd and Rh, wherein
   in the catalyst layer, the percentage content of Pt is in the range of 2.5 to 12 mass %, the percentage content of Pd is in the range of 0.4 to 2 mass %, and the percentage content of Rh is in the range of 0.06 to 1.5 mass %,
   the catalyst layer includes catalytic noble metal particles each of which is made of a Pt-Pd alloy, a Pt-Rh alloy or a Pt-Pd-Rh alloy,
   each of the catalytic noble metal particles has a core portion and an outer peripheral portion that surrounds the core portion, and
   the percentage content of Pt at the outer peripheral portion is lower than that at the core portion.

2. The gas sensor element as set forth in claim 1, wherein in the catalyst layer, the percentage content of Pt is in the range of 3 to 4.5 mass %, the percentage content of Pd is in the range of 0.8 to 1.2 mass %, and the percentage content of Rh is in the range of 0.2 to 0.3 mass %.

3. The gas sensor element as set forth in claim 1, wherein each of the catalytic noble metal particles is made of a Pt-Pd-Rh alloy.

4. The gas sensor element as set forth in claim 1, wherein for each of the catalytic noble metal particles, the percentage content of Pt at the core portion of the catalytic noble metal particle is higher than or equal to 50 mass %.

5. The gas sensor element as set forth in claim 4, wherein for each of the catalytic noble metal particles, the percentage content of Pt at the core portion of the catalytic noble metal particle is higher than or equal to 65 mass %.

6. A gas sensor characterized by comprising the gas sensor element as set forth in claim 1.

* * * * *